(12) United States Patent
Gupta et al.

(10) Patent No.: US 8,012,753 B2
(45) Date of Patent: Sep. 6, 2011

(54) METHODS AND COMPOSITIONS FOR REGROWTH OF CRYOPRESERVED CONIFER EMBRYOS

(75) Inventors: Pramod K. Gupta, Federal Way, WA (US); Bonnie Larson, Granite Falls, WA (US); Doris Budworth, Puyallup, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 1589 days.

(21) Appl. No.: 10/875,666

(22) Filed: Jun. 24, 2004

(65) Prior Publication Data

US 2005/0026282 A1 Feb. 3, 2005

Related U.S. Application Data

(60) Provisional application No. 60/491,373, filed on Jul. 30, 2003.

(51) Int. Cl.
*C12N 5/00* (2006.01)
(52) U.S. Cl. ......... 435/422; 435/420; 435/431; 435/1.1; 435/1.3; 436/18
(58) Field of Classification Search .................. 435/422, 435/420, 431, 1.1, 1.3; 436/18
See application file for complete search history.

(56) References Cited

U.S. PATENT DOCUMENTS

| 6,682,931 B2 * | 1/2004 | Becwar et al. ................ 435/422 |
| 2003/0031998 A1 * | 2/2003 | Kadkade ............................ 435/2 |

FOREIGN PATENT DOCUMENTS

| CA | 2223959 A1 | 12/1996 |
| CA | 2309448 A1 | 11/2000 |

OTHER PUBLICATIONS

Plant culture a Practical approach Dixon 1985 3 pages.*

Hansen et al. Recent advances in the transformation of plants Trends in Plant Science reviews. Jun. 1999, vol. 4, No. 6 pp. 226-231.*
Chang Y et al., "Cold acclimation improves recovery of cryopreserved grass (*Zoysia* and *Lolium* Sp.)," *CryoLetters* 21, 107-116 (2000).
Shibli RA et al., "Cryopreservation of 'Nabali' olive (Olea europen L.) somatic embryos by encapsulation-dehydration and encapsulation-vitrification," *CryoLetters* 21, 357-366 (2000).
Shibli RA et al., "Cryopreservation of black iris (iris nigricans) somatic embryos by encapsulation-dehydration," *CryoLetters* 21, 39-46 (2000).
Pennycooke JC et al., "Medium alterations improve regrowth of sweet potato (Ipomoea batatas [L] Lam.) shoot tips cryopreserved by vitrification and encapsulation-dehydration," *CryoLetters* 22, 381-389 (2001).
Zhang YX et al., "Pregrowth-desiccation: A simple and efficient procedure for the cryopreservation of rice (Oryza sativa L.) embryonic suspension cells," *CryoLetters* 22, 221-228 (2001).
Benson, E.E., "Cryopreservation," in R.A. Dixon and A. Gonzales (eds.), "Plant Cell Culture. A Practical Approach," Oxford University Press, London, 1994, pp. 147-167.
Gupta, P.K., et al., "Somatic Embryo Development in Liquid Medium for Large-Scale Propagation of Conifer Trees," Congress on In Vitro Biology, Portland, Oregon, May 31-Jun. 4, 2003, p. 14-A.
Mathur, G. et al., Cryopreservation of embryogenic culture of Pinus roxburghii, Biologic Plantarum 46 (2); 205-210, 2003.
Gupta, P.K. and D.J. Durzan, Shoot multiplication from mature trees of Douglas-fir (Pseudotsuga menziesii) and sugar pine (Pinus lambertiana), Plant Cell Reports 4:177-179, 1985.
Nagmani, R., et al., "Anatomical Comparison of Somatic and Zygotic Embryogeny in Conifers," in S.M. Jain et al. (eds.), vol. 1, "Somatic Embryogenesis in Woody Plants," Series: Forestry Sciences, 1995, vol. 44, pp. 23-48.

* cited by examiner

*Primary Examiner* — Annette Para
(74) *Attorney, Agent, or Firm* — Christensen O'Connor Johnson Kindness PLLC

(57) ABSTRACT

The present invention provides methods for regrowth of conifer embryogenic cells. The methods comprise the steps of (a) contacting cryopreserved conifer embryogenic cells with a liquid transition medium, and (b) culturing the contacted conifer embryogenic cells in a regrowth medium to generate regrowth of the conifer embryogenic cells. Generally, the cryopreserved conifer embryogenic cells are contacted with the liquid transition medium for less than about 24 hours, such as for about one hour.

8 Claims, No Drawings

METHODS AND COMPOSITIONS FOR REGROWTH OF CRYOPRESERVED CONIFER EMBRYOS

CROSS REFERENCE TO RELATED APPLICATION

The present application claims the benefit of U.S. Provisional Application No. 60/491,373, filed Jul. 30, 2003.

FIELD OF THE INVENTION

The present invention relates to methods and composition for regrowth of cryopreserved conifer embryos.

BACKGROUND OF THE INVENTION

The demand for coniferous trees, such as pines and firs, to make wood products continues to increase. One proposed solution to this problem is to identify individual trees that possess desirable characteristics, such as a rapid rate of growth, and produce numerous, genetically identical, clones of the superior trees by somatic cloning.

Somatic cloning is the process of creating genetically identical trees from tree tissue other than the male and female gametes. Plant cell suspension cultures are widely used for regeneration of somatic embryos. Cryopreservation allows these cultures to be stored potentially indefinitely with minimal maintenance and risks. However, there is a need for efficient methods for regrowth of cryopreserved conifer embryogenic cultures that are amenable to automated or semi-automated processes. The present invention addresses this need.

SUMMARY OF THE INVENTION

The present invention provides methods for regrowth of conifer embryogenic cells. The methods comprise the steps of (a) contacting cryopreserved conifer embryogenic cells with a liquid transition medium, and (b) culturing the contacted conifer embryogenic cells in a regrowth medium to generate regrowth of the conifer embryogenic cells. The cryopreserved conifer embryogenic cells may be contacted with the liquid transition medium for up to about 96 hours. Typically, the cryopreserved conifer embryogenic cells are contacted with the liquid transition medium for less than about 24 hours, such as for about one hour. Typically, the embryogenic cells are cultured in the regrowth medium for a period between about 1 week and about 10 weeks.

The regrowth medium may be a solid medium, a semi-solid medium, or a liquid medium. In some embodiments, the transition medium and the regrowth medium comprise a principal carbohydrate source selected from the group of maltose, glucose, or a combination thereof. The transition medium or the regrowth medium may optionally contain abscisic acid.

DETAILED DESCRIPTION OF THE PREFERRED EMBODIMENT

Unless specifically defined herein, all terms used herein have the same meaning as they would to one skilled in the art of the present invention.

Unless stated otherwise, all concentration values that are expressed as percentages are weight per volume percentages.

The present invention provides methods for regrowth of conifer embryogenic cells. The methods comprise the steps of (a) contacting cryopreserved conifer embryogenic cells with a liquid transition medium for less than about 24 hours, and (b) culturing the contacted conifer embryogenic cells in a regrowth medium to generate regrowth of the conifer embryogenic cells. In some embodiments, the conifer embryogenic cells are contacted with the liquid transition medium for about one hour. The methods of the invention are applicable to any member of the order Coniferales, such as Douglas fir, Norway spruce, members of the genus *Abies* (e.g., Noble fir), and members of the genus *Pinus*, such as Loblolly pine (*Pinus taeda*).

As used herein, the terms "embryogenic cells" refers to any cells, including cells that are organized to form a tissue or an organ, derived from a plant of the order Coniferales, that are capable of producing one or more conifer somatic embryos. Thus, the term "embryogenic cells" includes, for example, conifer embryonal suspensor masses (ESMs). An exemplary method for producing conifer embryogenic cells is described in EXAMPLE 1.

As used herein, the term "cryopreservation" refers to the storage of cells, such as conifer embryogenic cells, at ultra-low temperatures, usually in liquid nitrogen ($-196°$ C.). The cells remain viable throughout the cryopreservation process due to the application of cryoprotective procedures. Exemplary cryoprotection and cryopreservation methods are described in EXAMPLE 1.

In the first step of the methods of the invention, cryopreserved conifer embryogenic cells are contacted with a liquid transition medium. Typically, a cryopreserved culture of conifer embryogenic cells is rapidly thawed and transferred to a solid support on which the fluid is allowed to drain. For example, the culture may be transferred to a filter paper that has been placed on a dry pad or blotter, as described in EXAMPLE 1. The thawed and drained embryogenic cells are then contacted with the liquid transition medium. For example, thawed and drained embryogenic cells may be transferred to a liquid transition medium-soaked pad in a petri dish, as described in EXAMPLE 1.

The liquid transition medium generally includes inorganic salts and organic nutrient materials. For example, the induction medium may include maltose, sucrose, glucose, or a combination thereof, as a principal carbohydrate source. Examples of useful carbohydrate concentrations are within the range from about 1% to about 5%, such as about 3%. The osmolality of the liquid transition medium is typically between about 100 mM/kg and about 250 mM/kg, such as about 150 mM/kg. The liquid transition medium typically includes growth hormones. Examples of hormones that can be included in the liquid transition medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/l to 200 mg/l. Cytokinins can be utilized, for example, at a concentration of from 0.1 mg/l to 10 mg/l.

The transition medium may optionally include the hormone abscisic acid. Abscisic acid is a sesquiterpenoid plant hormone that is implicated in a variety of plant physiological processes (see, e.g., Milborrow (2001) *J. Exp. Botany* 52:1145-1164; Leung & Giraudat (1998) *Ann. Rev. Plant Physiol. Plant Mol. Biol.* 49:199-123). In some embodiments of the methods of the invention, the concentration of abscisic acid in the liquid development medium is between 1 mg/l and 200 mg/l, such as between 5 mg/l and 50 mg/l. Examples of suitable transition media have the compositions of $BM_{1-4}$, which are set forth in EXAMPLE 1.

The embryogenic cells are generally contacted with the transition medium for less than 24 hours, such as for about 3 hours, or about 1 hour. However, they may also be contacted with the liquid transition for longer periods of time, such as up to about 96 hours.

In the second step of the methods of the invention, the cryopreserved embryogenic cells are cultured in or on a regrowth medium to generate regrowth of the conifer embryogenic cells.

The regrowth medium may be a solid medium, a semi-solid medium, or a liquid medium. The regrowth medium generally includes inorganic salts and organic nutrient materials. For example, the regrowth medium may include maltose, sucrose, glucose, or a combination thereof, as a principal carbohydrate source. Examples of useful carbohydrate concentrations are within the range from about 1% to about 5%, such as about 3%. In some embodiments, the regrowth medium includes maltose at a concentration within the range from about 1% to about 5% and/or glucose at a concentration within the range from about 1% and 3%.

The osmolality of the regrowth medium is typically between about 100 mM/kg and about 250 mM/kg, such as about 150 mM/kg. The regrowth medium typically includes growth hormones, such as 2,4-D, BAP, or kinetin, at concentrations similar to those present in the liquid transition medium. The regrowth medium may optionally include the hormone abscisic acid. In some embodiments of the invention, solid regrowth media do not contain abscisic acid.

The composition of the regrowth medium may be identical to the composition of the transition medium. Thus, examples of suitable liquid regrowth media have the compositions of $BM_{1-4}$, which are set forth in EXAMPLE 1. Examples of suitable solid regrowth media have the composition of $BM_{5-8}$, which are set forth in EXAMPLE 1.

Cryopreserved embryogenic cells may be cultured in, or on, regrowth medium for a period between about 1 week and about 10 weeks, such as between about 3 to about 8 weeks, at a temperature of from 10° C. to 30° C., such as from 15° C. to 25° C., or such as from 20° C. to 23° C.

The invention provides simple and reliable methods for regrowing conifer embryogenic cells after cryopreservation. For example, the methods of the invention produce a similar or higher amount of regrowth of cryopreserved conifer embryogenic cells embryos than an equivalent method in which the embryogenic cells are first contacted with a solid transition medium that is otherwise identical to the liquid transition medium. In some embodiments, a similar amount of regrowth of embryogenic cells is obtained using liquid or solid regrowth media, as shown in EXAMPLES 1 and 2. In addition, high regrowth yields are obtained in the absence of abscisic acid in either the liquid transition medium or the regrowth medium. For example, high regrowth yields are obtained using solid regrowth media without abscisic acid, as shown in EXAMPLES 1 and 2.

Moreover, the use of liquid transition medium and, optionally a liquid regrowth medium, according to the invention simplifies the production of cotyledonary embryos because liquid media are easier to prepare, to store, and to use in automated production procedures.

The following examples merely illustrate the best mode now contemplated for practicing the invention, but should not be construed to limit the invention.

EXAMPLE 1

This Example shows a representative method of the invention for regrowing a cryopreserved culture of Loblolly pine somatic embryos.

Methods: Female gametophytes containing zygotic embryos were removed from seeds of 8 genotypes four to five weeks after fertilization. The seed coats were removed but the embryos were not further dissected out of the surrounding gametophyte other than to excise the nucellar end. The cones were stored at 4° C. until used. Immediately before removal of the immature embryos the seeds were sterilized utilizing an initial washing and detergent treatment followed by a ten minute sterilization in 15% $H_2O_2$. The explants were thoroughly washed with sterile distilled water after each treatment.

Sterile gametophytes with intact embryos were placed on a solid induction medium and held in an environment at 22° C.-25° C. with a 24 hour dark photoperiod for a time of 3 to 5 weeks. The induction medium had the composition of $BM_1$ shown in Table 1, except that it contained 1600 mg/l of GELRITE and the concentrations of 2,4-D, BAP, and kinetin were raised to 3.3 mg/l, 0.4 mg/l, and 0.4 mg/l, respectively. The length of time depends on the particular genotype being cultured. At the end of this time a white mucilaginous mass (embryonal suspensor mass, ESM) formed in association with the original explants. Microscopic examination typically revealed numerous early stage embryos associated with the mass.

ESMs generated in the induction stage were placed on liquid maintenance and multiplication medium. This differs from the induction medium in that it contains no gellan gum and the concentrations of 2,4-D, BAP, and kinetin were reduced to 1.1 mg/l, 0.1 mg/l, and 0.1 mg/l, respectively. The temperature and photoperiod were again 22 to 25° C. with 24 hours in the dark.

For cryoprotection, 7 day old suspension cultures were settled for 15 to 20 minutes, after which the supernatant was removed. 5 ml of settled cells were transferred to 25 ml of a first cryoprotection medium in a 250 ml Erlenmeyer flask at a density of 1:9. The first cryoprotection medium has the same composition as the maintenance medium, except that it additionally contains 0.2 M sorbitol. After 24 hours on a shaker (rotating at 100 rpm), 5 ml of settled cells were transferred to a second cryoprotection medium at a density of 1:9. The second cryoprotection medium has the same composition as the first cryoprotection medium, except that the concentration of sorbitol is increased to 0.4 M. After 24 hours on a shaker (rotating at 100 rpm), the flask was placed on ice, and DMSO was added 10 times under continuous shaking over a 30 minute period to a final concentration of 5% (v/v).

For cryopreservation, the cell density was adjusted to 30% (v/v) packed cell volume by removing supernatant. 1.0 ml aliquots of cell suspension were dispensed into 1.2 ml cryovials. The cryovials were placed into canisters standing in crushed ice. The canisters were loaded into a CryoMed programmable freezer. The temperature was reduced to minus 35° C. at a cooling rate from 0.4° C. to 1° C. per minute. The canister was then placed into a rack of a cryostorage tank, which was stored in liquid nitrogen immersion phase.

For recovery of cryopreserved cultures, the cryovials were placed into sterile water warmed to 37° C. in a water bath and agitated until all the ESM has thawed. The cryovials were then transferred to a rack at room temperature. Each vial was wiped with a 70% solution of isopropyl alcohol. The contents of each cryovial was poured onto a sterile Whatman #2 filter paper on a small Pall-Gelman blotter plate. After the fluid has drained, the filter papers were transferred to a pad in a petri soaked with liquid transition medium (composition $BM_1$, see Table 1). After an hour at room temperature, the filter papers were transferred either to a fresh pad soaked with liquid regrowth medium (composition $BM_1$) or to solid regrowth medium (composition $BM_5$, see Table 1).

TABLE 1

Composition of Media for Cryopreserved Embryogenic Cultures

| Constituent | $BM_1$ (mg/l) | $BM_2$ (mg/l) | $BM_3$ (mg/l) | $BM_4$ (mg/l) | $BM_5$ (mg/l) | $BM_6$ (mg/l) | $BM_7$ (mg/l) | $BM_8$ (mg/l) |
|---|---|---|---|---|---|---|---|---|
| $NH_4NO_3$ | 150 | 150 | 150 | 150 | 150 | 150 | 150 | 150 |
| $KNO_3$ | 909.9 | 909.9 | 909.9 | 909.9 | 909.9 | 909.9 | 909.9 | 909.9 |
| $Ca(NO_3)_2 \cdot 4H_2O$ | 236.15 | 236.15 | 236.15 | 236.15 | 236.15 | 236.15 | 236.15 | 236.15 |
| $MgSO_4 \cdot 7H_2O$ | 246.5 | 246.5 | 246.5 | 246.5 | 246.5 | 246.5 | 246.5 | 246.5 |
| $Mg(NO_3)_2 \cdot 6H_2O$ | 256.5 | 256.5 | 256.5 | 256.5 | 256.5 | 256.5 | 256.5 | 256.5 |
| $MgCl_2 \cdot 6H_2O$ | 50 | 50 | 50 | 50 | 50 | 50 | 50 | 50 |
| $KH_2PO_4$ | 136 | 136 | 136 | 136 | 136 | 136 | 136 | 136 |
| $CaCl_2 \cdot 2H_2O$ | 50 | 50 | 50 | 50 | 50 | 50 | 50 | 50 |
| KI | 4.15 | 4.15 | 4.15 | 4.15 | 4.15 | 4.15 | 4.15 | 4.15 |
| $H_3BO_3$ | 15.5 | 15.5 | 15.5 | 15.5 | 15.5 | 15.5 | 15.5 | 15.5 |
| $MnSO_4 \cdot H_2O$ | 10.5 | 10.5 | 10.5 | 10.5 | 10.5 | 10.5 | 10.5 | 10.5 |
| $ZnSO_4 \cdot 7H_2O$ | 14.4 | 14.4 | 14.4 | 14.4 | 14.4 | 14.4 | 14.4 | 14.4 |
| $Na_2MoO_4 \cdot 2H_2O$ | 0.125 | 0.125 | 0.125 | 0.125 | 0.125 | 0.125 | 0.125 | 0.125 |
| $CuSO_4 \cdot 5H_2O$ | 0.125 | 0.125 | 0.125 | 0.125 | 0.125 | 0.125 | 0.125 | 0.125 |
| $CoCl_2 \cdot 6H_2O$ | 0.125 | 0.125 | 0.125 | 0.125 | 0.125 | 0.125 | 0.125 | 0.125 |
| $FeSO_4 \cdot 7H_2O$ | 27.87 | 27.87 | 27.87 | 27.87 | 27.87 | 27.87 | 27.87 | 27.87 |
| $Na_2EDTA$ | 37.26 | 37.26 | 37.26 | 37.26 | 37.26 | 37.26 | 37.26 | 37.26 |
| Nicotinic acid | 0.5 | 0.5 | 0.5 | 0.5 | 0.5 | 0.5 | 0.5 | 0.5 |
| Pyridoxine•HCl | 0.5 | 0.5 | 0.5 | 0.5 | 0.5 | 0.5 | 0.5 | 0.5 |
| Thiamine•HCl | 1 | 1 | 1 | 1 | 1 | 1 | 1 | 1 |
| Glycine | 2 | 2 | 2 | 2 | 2 | 2 | 2 | 2 |
| Myo-Inositol | 200 | 200 | 200 | 200 | 200 | 200 | 200 | 200 |
| Casein hydrolysate | 500 | 500 | 500 | 500 | 500 | 500 | 500 | 500 |
| L-Glutamine | 1000 | 1000 | 1000 | 1000 | 1000 | 1000 | 1000 | 1000 |
| Maltose | 30000 | | | 10000 | 30000 | | | 10000 |
| Glucose | | 15000 | | 10000 | | 15000 | | 10000 |
| Sucrose | | | 30000 | | | | 30000 | |
| GELRITE | | | | | 1600 | 1600 | 1600 | 1600 |
| Abscisic acid | 1 | 1 | 1 | 1 | | | | |
| 2,4-D | 1.1 | 1.1 | 1.1 | 1.1 | 1.1 | 1.1 | 1.1 | 1.1 |
| BAP | 0.1 | 0.1 | 0.1 | 0.1 | 0.1 | 0.1 | 0.1 | 0.1 |
| Kinetin | 0.1 | 0.1 | 0.1 | 0.1 | 0.1 | 0.1 | 0.1 | 0.1 |
| pH adjusted to 5.7 | | | | | | | | |

Results: After 8 days in or on regrowth medium, cultures from all vials were growing ESMs. After 18 days, the samples were weighed. The weight of the plate without the filter paper and ESMs was subtracted from the weight of the plate with the filter paper and ESMs to provide the weight of the ESMs. The average ESMs weights obtained was about 777.5 mg for regrowth on solid or in liquid regrowth media.

EXAMPLE 2

This Example shows a comparison of the recovery of Loblolly pine somatic embryos after contacting the cryopreserved conifer embryogenic cells with four different liquid transition media, followed by four different liquid or solid regrowth media.

Loblolly pine embryogenic cultures of eight different genotypes were produced and cryopreserved as described in EXAMPLE 1. For recovery of cryopreserved cultures, eight cryovials of each genotype were placed into sterile water warmed to 37° C. in a water bath and agitated until all the ice has melted. The cryovials were then transferred to a rack at room temperature. Each vial was wiped with a 70% solution of isopropyl alcohol.

The contents of 2 vials of each genotype were randomly chosen to be placed on each of four liquid transition media with compositions of $BM_{1-4}$ (see Table 1). One vial of ESMs on each liquid transition medium was transferred to a liquid regrowth medium with the identical composition as the liquid transition medium, the other vial was transferred to a solid regrowth medium with an identical composition as the liquid transition medium, except lacking abscisic acid and containing 1600 mg/l gellan gum (compositions $BM_{5-8}$, see Table 1), as shown in Table 2.

In a laminar flow, each vial was poured onto a sterile Whatman #2 filter paper on dry pads in sterile petri plates. After the culture had drained, the filter paper was transferred to a new petri plate with a pad soaked in about 18 ml of one of the four liquid transition media. After one hour, the filter papers were transferred to a fresh plate containing solid regrowth medium or a fresh plate containing a pad soaked in liquid regrowth medium. All plates were wrapped in parafilm and placed into crispers for one week at room temperature.

Results: After 8 days in, or on, regrowth medium, all samples were growing ESMs. After 18 days, the samples were weighed. The weight of the plate without the filter paper and ESMs was subtracted from the weight of the plate with the filter paper and ESMs to provide the weight of the ESMs. The average ESMs weights obtained for all eight genotypes combined are shown in Table 2.

TABLE 2

Average ESM Weight Using Different Media

| Composition of Media | | |
|---|---|---|
| Transition Medium | Regrowth Medium | ESM weight (mg) |
| $BM_1$ | $BM_1$ | 793.4 |
| $BM_2$ | $BM_2$ | 764.0 |
| $BM_3$ | $BM_3$ | 706.1 |
| $BM_4$ | $BM_4$ | 662.9 |
| $BM_1$ | $BM_5$ | 891.6 |
| $BM_2$ | $BM_6$ | 876.5 |
| $BM_3$ | $BM_7$ | 634.2 |
| $BM_4$ | $BM_8$ | 890.9 |

For all genotypes combined, an average weight of 823.2803 mg of ESMs was obtained from growth on solid regrowth media $BM_{5-8}$, and an average weight of 731.6094 mg of ESMs for growth on liquid regrowth media $BM_{1-4}$. The difference in weight between growth on liquid regrowth media and solid regrowth media was not statistically significant.

There was also no statistically significant difference between the amount of regrowth obtained using maltose, glucose, or a combination of maltose and glucose (i.e., $BM_1$, $BM_2$, and $BM_4$) in the regrowth medium. However, the amount or regrowth obtained using sucrose in the regrowth medium (i.e., $BM_2$) was significantly lower (p=0.1325).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for regrowth of cryopreserved Pinus embryogenic cells, comprising the steps of:
   (a) contacting cryopreserved Pinus embryogenic cells with a liquid transition medium for at least one hour, wherein the transition medium comprises abscisic acid; and
   (b) culturing the contacted Pinus embryogenic cells in, or on, a regrowth medium to produce regrowth of the Pinus embryogenic cells; wherein the transition medium and the regrowth medium comprise one or more carbohydrate sources selected from the group consisting of maltose at a concentration from about 1% to about 3%, and glucose at a concentration from about 1% to about 1.5%.

2. The method of claim 1, wherein the Pinus embryogenic cells are contacted with the liquid transition medium for less than about 24 hours.

3. The method of claim 1, wherein the regrowth medium is a solid medium.

4. The method of claim 1, wherein the regrowth medium is a liquid medium.

5. The method of claim 1, wherein the regrowth medium comprises glucose at a concentration of about 1.5%.

6. The method of claim 1, wherein the regrowth medium comprises maltose at a concentration of about 3%.

7. The method of claim 1, wherein the regrowth medium comprises glucose and maltose, wherein the concentration of glucose is about 1% and the concentration of maltose is about 1%.

8. The method of claim 1, wherein the Pinus embryogenic cells are cultured in regrowth medium for a period between about 1 week and about 10 weeks.

* * * * *